US008933038B2

(12) United States Patent
Sugiyama

(10) Patent No.: US 8,933,038 B2
(45) Date of Patent: Jan. 13, 2015

(54) **METHOD OF TREATING CANCER WITH AN HLA-A*3303-RESTRICTED WT1 PEPTIDE AND PHARMACEUTICAL COMPOSITION COMPRISING THE SAME**

(71) Applicant: International Institute of Cancer Immunology, Inc., Osaka (JP)

(72) Inventor: Haruo Sugiyama, Osaka (JP)

(73) Assignee: International Institute of Cancer Immunology, Inc., Osaka (JP)

( * ) Notice: Subject to any disclaimer, the term of this patent is extended or adjusted under 35 U.S.C. 154(b) by 0 days.

(21) Appl. No.: 14/145,221

(22) Filed: Dec. 31, 2013

(65) Prior Publication Data

US 2014/0193442 A1 Jul. 10, 2014

Related U.S. Application Data

(62) Division of application No. 13/411,453, filed on Mar. 2, 2012, which is a division of application No. 12/280,268, filed as application No. PCT/JP2007/053176 on Feb. 21, 2007.

(30) Foreign Application Priority Data

Feb. 22, 2006 (JP) ................ 2006-045287

(51) Int. Cl.
| | |
|---|---|
| C07K 7/06 | (2006.01) |
| C07K 14/47 | (2006.01) |
| C07K 19/00 | (2006.01) |
| C12N 15/09 | (2006.01) |
| C12N 15/06 | (2006.01) |
| C12N 15/11 | (2006.01) |
| C12N 15/12 | (2006.01) |
| C12N 15/63 | (2006.01) |
| C12N 5/00 | (2006.01) |
| C12N 5/02 | (2006.01) |
| C12N 5/071 | (2010.01) |
| C12N 5/0783 | (2010.01) |
| A61K 38/00 | (2006.01) |
| A61K 38/08 | (2006.01) |
| G01N 33/50 | (2006.01) |
| G01N 33/574 | (2006.01) |
| A61K 39/00 | (2006.01) |

(52) U.S. Cl.
CPC .............. *A61K 38/08* (2013.01); *A61K 38/00* (2013.01); *C07K 14/4748* (2013.01); *G01N 33/505* (2013.01); *G01N 33/574* (2013.01); *C07K 7/06* (2013.01); *A61K 39/00* (2013.01)
USPC ....... 514/19.3; 514/19.4; 514/19.5; 514/19.6; 514/44 R; 435/29; 435/320.1; 435/325; 435/375; 530/328; 536/23.5; 424/185.1

(58) Field of Classification Search
CPC ....... A61K 38/00; A61K 38/08; A61K 39/00; C07K 14/4748; C07K 7/06; G01N 33/505; G01N 33/574
USPC ................... 514/19.3, 19.4, 19.5, 19.6, 44 R; 424/184.1; 435/29, 320.1, 325, 375; 530/328; 536/23.5
See application file for complete search history.

(56) References Cited

U.S. PATENT DOCUMENTS

| | | | |
|---|---|---|---|
| 5,595,756 A * | 1/1997 | Bally et al. .................... 424/450 |
| 6,270,777 B1 | 8/2001 | Sokol et al. | |
| 6,344,436 B1 | 2/2002 | Smith et al. | |
| 6,797,695 B1 | 9/2004 | Itoh et al. | |
| 7,063,854 B1 | 6/2006 | Gaiger et al. | |
| 7,115,272 B1 | 10/2006 | Gaiger et al. | |
| 7,144,581 B2 | 12/2006 | Gaiger et al. | |
| 2003/0039635 A1 | 2/2003 | Gaiger et al. | |
| 2003/0072767 A1 | 4/2003 | Gaiger et al. | |
| 2003/0082196 A1 | 5/2003 | Gaiger et al. | |
| 2003/0095971 A1 | 5/2003 | Gaiger et al. | |
| 2003/0198622 A1 | 10/2003 | Gaiger et al. | |
| 2003/0211521 A1 | 11/2003 | Taylor-Papadimitriou | |
| 2003/0235557 A1 | 12/2003 | Gaiger et al. | |
| 2004/0126362 A1 | 7/2004 | Gaiger et al. | |
| 2004/0197892 A1 | 10/2004 | Moore et al. | |
| 2006/0121046 A1 | 6/2006 | Gaiger et al. | |
| 2007/0082860 A1 | 4/2007 | Sugiyama et al. | |

(Continued)

FOREIGN PATENT DOCUMENTS

| | | |
|---|---|---|
| EP | 1 550 453 A1 | 7/2005 |
| EP | 1 584 627 A1 | 10/2005 |

(Continued)

OTHER PUBLICATIONS

Michael B. Sporn, Chemoprevention of cancer,2000, Carcinogenesis, vol. 21 No. 3, pp. 535-530.*

(Continued)

*Primary Examiner* — Julie Ha
*Assistant Examiner* — Erinne Dabkowski
(74) *Attorney, Agent, or Firm* — Finnegan, Henderson, Farabow, Garrett & Dunner, L.L.P.

(57) ABSTRACT

Disclosed are: a peptide comprising an amino acid sequence composed of contiguous nine amino acid residues derived from a WT1 protein, wherein an amino acid residue at position 2 in the amino acid sequence is selected from the group consisting of Ala, Ile, Leu, Val, Phe, Tyr, Ser and Asp and an amino acid residue at position 9 in the amino acid sequence is Arg; a polynucleotide encoding the peptide; a pharmaceutical composition comprising the peptide; and a method of treating cancer using the peptide.

12 Claims, 8 Drawing Sheets

(56) References Cited

U.S. PATENT DOCUMENTS

| | | |
|---|---|---|
| 2008/0152631 A1 | 6/2008 | Sugiyama |
| 2010/0292160 A1 | 11/2010 | Sugiyama |

FOREIGN PATENT DOCUMENTS

| | | |
|---|---|---|
| EP | 1 731 605 A1 | 12/2006 |
| EP | 1 988 163 B1 | 6/2012 |
| JP | 4-503014 A | 6/1992 |
| WO | WO 91/07509 A1 | 5/1991 |
| WO | WO 00/18795 A2 | 4/2000 |
| WO | WO 01/25273 A3 | 4/2001 |
| WO | WO 02/14361 A2 | 2/2002 |
| WO | WO 02/28414 A1 | 4/2002 |
| WO | WO 03/037060 A2 | 5/2003 |
| WO | WO 2004/067716 A2 | 8/2004 |

OTHER PUBLICATIONS

Trisha Gura, Systems for Identifying New Drugs are Often Faulty, 1997, Science, vol. 278 No. 5340, pp. 1041-1042.*
Robert Auerbach, Angiogenesis assays: Problems and Pitfalls, 2000, Cancer and Metastasis Reviews, vol. 19, pp. 167-172.*
Stephen Neidle, Cancer Drug Design and Discovery, 2008, Elsevier/Academic Press, pp. 427-431.*
Rakesh K. Jain, Barriers to Drug Delivery in Solid Tumors, 1994, Scientific Journal, pp. 58-65.*
Azuma et al., "Ran, a Small GTPase Gene, Encodes Cytotoxic T Lymphocyte (CTL) Epitopes Capable of Inducing HLA-A33-Restricted and Tumor-Reactive CTLs in Cancer Patients," Clinical Cancer Research, 10:6695-6702 (2004).
Call et al., "Isolation and Characterization of a Zinc Finger Polypeptide Gene at the Human Chromosome 11 Wilms' Tumor Locus," Cell, 1990, vol. 60, pp. 509-520.
Elisseeva et al., "Humoral Immune Responses Against Wilms Tumor Gene WT1 Product in Patients with Hematopoietic Malignancies," Blood: 99:3272-3279 (2002).
Gaiger et al., "Immunity to WT1 in the Animal Model and in Patients with Acute Myeloid Leukemia," Blood, 96:1480-1489 (2000).
Gao et al., "Selective Elimination of Leukemic CD34+ Progenitor Cells by Cytotoxic T Lymphocytes Specific for TW1," Blood, 2000, vol. 95, No. 7, pp. 2198-2203.
Haber et al, "An Internal Deletion with an 11p13 Zinc Finger Gene Contributes to the Development of Wilms' Tumor," Cell, 1990, vol. 61, pp. 1257-1269.
Hossain et al., "Identification and Characterization of HLA-A*3303-Restricted, HIV Type 1 Pol- and Gag-Derived Cytotoxic T Cell Epitopes," Aids Research and Human Retroviruses, vol. 19, No. 6, pp. 503-510, (2003).
Inoue et al., "Wilms' Tumor Gene (TW1) Competes with Differentiation-Inducing Signal in Hematopoietic Progenitor Cells," Blood, 1998, vol. 91, No. 8, pp. 2969-2976.
Melief et al., "T-Cell Immunotherapy of Tumors by Adoptive Transfer of Cytotoxic T Lymphocytes and by Vaccinaction with Minimal Essential Eptiopes," Immunolgical Review, 1995, 146, pp. 167-177.
Menke, "The Wilms' Tumor 1 Gene: Oncogene or Tumor Suppressor Gene'?," International Review of Cytology, 1998, vol. 181, pp. 151-212, Review.
Ohminami et al., "HLA Class I-Restricted Lysis of Leukemia Cells by a CD8+ Cytotoxic T-Lymphocyte Clone Specific for WT1 Peptide," Blood, 2000, vol. 95, No. 1 pp. 286-293.
Oka et al., "Cancer Immunotherapy Targeting Wilms' Tumor Gene WT1 Product," The Journal of Immunology, 2000, vol. 164, pp. 1873-1880.
Oka et al., "Human Cytotoxic T-Lymphocyte Responses Specific for Peptides of the Wild-Type Wilms' Tumor Gene (WT1) Product," Immunogenetics, 2000, vol. 51, pp. 99-107.
Oka et al., "WT1 as a Novel Target Antigen for Cancer Immunotherapy," Current Cancer Drug Targets, 2:45-54 (2002).
Ritz, "Tumor Immunity: Will New Keys Unlock the Door'?," Journal of Clinical Oncology, 1994, vol. 12, No. 2, pp. 237-238.
Rosenfeld et al., "WT1 in Acute Leukemia, Chronic Myelogenous Leukemia and Myelodysplastic Syndrome: Therapeutic Potential of WT1 Targeted Therapies," Leukemia, 17:1301-1312 (2003).
Tsuboi et al., "Constitutive Expression of the Wilms' Tumor Gene WT1 Inhibits the Differentiation of Myeloid Progenitor Cells But Promotes Their Proliferation in Response to Granulocyte-Colony Stimulating Factor (G-CSF)," Leukemia Research, 1999, vol. 23, pp. 499-505.
Tsuboi et al., "Cytotoxic T-Lymphocyte Responses Elicited to Wilms' Tumor Gene WT1 Product by DNA Vaccination," Journal of Clinical Immunology, 2000, vol. 20, No. 3, pp. 195-202.
Yamagami et al., "Growth Inhibition of Human Leukemic Cells by WT1 (Wilms Tumor Gene) Antisense Oligodeoxynucleotides: Implications for the Involvement of WT1 in Leukemogenesis," Blood, 1996, vol. 87, No. 7, pp. 2878-2884.
International Preliminary Report on Patentability, PCT/JP2007/053176 (Sep. 4, 2008).
Supplementary European Search Report from the European Patent office in European Patent Application No. EP 07 71 4676, dated Feb. 12, 2010.
Extended European Search Report received from the European Patent Office in European Patent Application No. 11161436.8, dated Oct. 11, 2011 (6 pages).
Office Action dated Nov. 12, 2010 issue in European Application No. 07 714 676.9.
European Office Action dated Jul. 5, 2012, issued in European Application No. 11161436.8 (5 pages).
Extended European Search Report dated Sep. 27, 2012, issued in European Patent Application No. 12174393.4.
Office Action dated Apr. 10, 2013, issued in European Patent Application No. 11161436.8.
Office Action dated Jan. 31, 2012, issued in Chinese Patent Application No. 20078005970.9.
Office Action dated Feb. 23, 2011 issued in Chinese Patent Application No. 200780005970.9.
Office Action dated Sep. 7, 2010 issued in Chinese Application No. 200780005970.9.
Office Action dated Apr. 1, 2012, issued in the Chinese Patent Application No. 201110156927.0.
Office Action dated Oct. 11, 2010 issued in Russian Application No. 2008137635.
Correspondence forwarding and describing Office Action issued in Israeli Patent Application No. 193,026, dated Aug. 19, 2010 (3 pages).
Office Action dated Oct. 30, 2011, issued in Israeli Patent Application No. 193,026 (2 pages).
Correspondence forwarding and describing Office Action issued in Israeli Patent Application No. 193,026, dated Nov. 2, 2011 (4 pages).
Correspondence dated Aug. 30, 2012, forwarding and describing an Office Action dated Aug. 20, 2012, issued in Israeli Patent Application No. 218,172.
Office Action dated Feb. 10, 2012, issued in Australian Patent Application No. 2007218649.
Office Action dated May 8, 2012, issued in the Japanese Patent Application No. 2008-501735.
Office Action dated Nov. 30, 2012, issued in Vietnamese Patent Application No. 1-2008-02300.
Office Action dated Dec. 14, 2012, issued in Malaysian Patent Application No. PI20082861.
Office Action dated Feb. 26, 2013, issued in Japanese Patent Application No. 2008-501735.
Office Action issued in Egyptian Patent Application No. 2008081345.
Office Action dated Sep. 26, 2013, issued in Canadian Patent Application No. 2,638,122.
Office Action dated Sep. 25, 2013, issued in Korean Patent Application No. 10-2008-7020447.
U.S. Appl. No. 13/411,453: Non-Final Office Action mailed Nov. 15, 2013.
U.S. Appl. No. 13/411,453: Response to Restriction Requirement filed Oct. 21, 2013.
U.S. Appl. No. 13/411,453: Restriction Requirement mailed Sep. 23, 2013.

(56) References Cited

OTHER PUBLICATIONS

U.S. Appl. No. 12/280,268: Reply to Non-Final Office Action filed Oct. 21, 2013.
U.S. Appl. No. 12/280,268: Non-Final Office Action mailed Aug. 6, 2011.
U.S. Appl. No. 12/280,268: Amendment and Response under 37 C.F.R. § 1.114 filed Aug. 31, 2012.
U.S. Appl. No. 12/280,268: Advisory Action mailed Jul. 25, 2012.
U.S. Appl. No. 12/280,268: Amendment After Final filed Jul. 18, 2012.
U.S. Appl. No. 12/280,268: Final Office Action mailed May 2, 2012.
U.S. Appl. No. 12/280,268: Reply to Non-Final Office Action filed Feb. 23, 2011.
U.S. Appl. No. 12/280,268: Non-Final Office Action mailed Oct. 27, 2011.
U.S. Appl. No. 12/280,268: Reply to Restriction Requirement filed Oct. 3, 2011.
U.S. Appl. No. 12/280,268: Restriction Requirement mailed Sep. 9, 2011.
Auerbach, "Angiogenesis assays: Problems and pitfalls," *Cancer and Metastasis Reviews*, 19: 167-172 (2000).
Gura, "Cancer Models: Systems for Identifying New Drugs are Often Faulty," *Science*, vol. 278, No. 5340, pp. 1041-1042 (1997).
Jain, "Barriers to Drug Delivery in Solid Tumors," *Scientific American*, pp. 58-65 (Jul. 1994).
Neidle, "Cancer Drug Design and Discovery," Elsevier/Academic Press, pp. 427-431 (2008).
Sporn at al., "Chemoprevention of cancer," *Carcinogenesis*, vol. 21, No. 3, pp. 525-530 (2000).
U.S. Appl. No. 12/280,268: Non-Final Office Action mailed Aug. 6, 2013.
U.S. Appl. No. 12/280,268: Reply to Non-Final Office Action filed Feb. 23, 2012.
U.S. Appl. No. 12/280,268: Final Office Action mailed Dec. 20, 2013.
U.S. Appl. No. 12/280,268: Reply to Final Office Action filed Feb. 7, 2014.
U.S. Appl. No. 13/411,453: Reply to Non-Final Office Action filed Feb. 3, 2014.
Office Action dated May 29, 2014, issued in Indian Patent Application No. 4345/CHENP/2008.

* cited by examiner

SEQUENCE LISTING

<160> NUMBER OF SEQ ID NOS: 5

<210> SEQ ID NO 1
<211> LENGTH: 449
<212> TYPE: PRT
<213> ORGANISM: Homo sapiens

<400> SEQUENCE: 1

Met Gly Ser Asp Val Arg Asp Leu Asn Ala Leu Leu Pro Ala Val Pro
 1               5                  10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

```
Gly Ser Leu Gly Gly Pro Ala Pro Pro Ala Pro Pro Pro Pro
     50                  55                  60

Pro Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Val His Phe
             85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
                115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
                180                 185                 190

Tyr Ser Val Pro Pro Val Tyr Gly Cys His Thr Pro Thr Asp Ser
            195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
                260                 265                 270

Ser Asp Asn His Thr Thr Pro Ile Leu Cys Gly Ala Gln Tyr Arg Ile
                275                 280                 285

His Thr His Gly Val Phe Arg Gly Ile Gln Asp Val Arg Arg Val Pro
                290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
                340                 345                 350

Tyr Gln Cys Asp Phe Lys Asp Cys Glu Arg Arg Phe Ser Arg Ser Asp
                355                 360                 365

Gln Leu Lys Arg His Gln Arg Arg His Thr Gly Val Lys Pro Phe Gln
370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
                420                 425                 430

Arg His His Asn Met His Gln Arg Asn Met Thr Lys Leu Gln Leu Ala
                435                 440                 445

Leu
```

```
<210> SEQ ID NO 2
<211> LENGTH: 9
<212> TYPE: PRT
<213> ORGANISM: Homo sapiens

<400> SEQUENCE: 2

Leu Ser His Leu Gln Met His Ser Arg
 1               5

<210> SEQ ID NO 3
<211> LENGTH: 9
<212> TYPE: PRT
<213> ORGANISM: Homo sapiens

<400> SEQUENCE: 3

Phe Ser Arg Ser Asp Gln Leu Lys Arg
 1               5

<210> SEQ ID NO 4
<211> LENGTH: 9
<212> TYPE: PRT
<213> ORGANISM: Homo sapiens

<400> SEQUENCE: 4

Ser Asp Gln Leu Lys Arg His Gln Arg
 1               5

<210> SEQ ID NO 5
<211> LENGTH: 9
<212> TYPE: PRT
<213> ORGANISM: Homo sapiens

<400> SEQUENCE: 5

Thr Ser Glu Lys Pro Phe Ser Cys Arg
 1               5
```

METHOD OF TREATING CANCER WITH AN HLA-A*3303-RESTRICTED WT1 PEPTIDE AND PHARMACEUTICAL COMPOSITION COMPRISING THE SAME

CROSS REFERENCE TO RELATED APPLICATIONS

This is a divisional application of U.S. patent application Ser. No. 13/411,453, filed Mar. 2, 2012, which is a divisional application of U.S. patent application Ser. No. 12/280,268, whose 35 U.S.C. §371(c) date is Aug. 2, 2010, which is a national stage of International Application No. PCT/JP2007/053176, filed Feb. 21, 2007, all of which claim priority to Japanese Patent Application No. 2006-045287, filed Feb. 22, 2006, and the entire disclosures of all of which are incorporated herein by reference.

TECHNICAL FIELD

The present invention relates to an HLA-A*3303-restricted peptide, specifically a peptide comprising an amino acid sequence consisting of 9 contiguous amino acids from a WT1 protein, wherein an amino acid at position 2 of the amino acid sequence is selected from the group consisting of Ala, Ile, Leu, Val, Phe, Tyr, Ser and Asp, and an amino acid at position 9 is Arg. Furthermore, the present invention relates to a polynucleotide encoding the peptide, a pharmaceutical composition for the treatment or prevention of a cancer comprising the same, and the like.

BACKGROUND

WT1 gene (Wilms' tumor 1 gene) was identified as a gene responsible for Wilms tumor which is a renal cancer in children (Non-patent Documents 1 and 2). WT1 is a transcription factor having a zinc finger structure. At the beginning, the WT1 gene was considered to be a tumor suppressor gene. However, subsequent studies (Non-patent Documents 3, 4, 5 and 6) showed that the WT1 gene rather functions as an oncogene in hematopoietic tumors and solid cancers.

The WT1 gene is expressed at high levels in many types of malignant tumors. It has been examined whether or not the WT1 gene product free of mutations, which is an autologous protein, has immunogenicity in a living body. The results revealed that the protein derived from the WT1 gene which is expressed at high levels in tumor cells is fragmented through intracellular processing, the resulting peptides form complexes with MHC class I molecules, and the complexes are presented on the surfaces of cells, and that CTLs recognizing such complexes can be induced by peptide vaccination (Non-patent Documents 7, 8 and 9). It was also shown that in a mouse immunized with a WT1 peptide or a WT1 cDNA, transplanted tumor cells expressing a WT1 gene are rejected with a high probability (Non-patent Documents 7 and 10), while normal tissues expressing physiologically the WT1 gene are not damaged by the induced CTLs (Non-patent Document 7). It was shown in in vitro experiments using human cells that when Db126 peptide or WH187 peptide (amino acids 187-195 of SEQ ID No: 1, SLGEQQYSV) having a high ability to bind to an HLA-A*0201 molecule, which is one of human MHC class I molecules, is used to stimulate human peripheral blood mononuclear cells having HLA-A*0201, WT1-specific CTLs are induced, the induced CTLs have a cytotoxic activity specific for tumor cells expressing endogenously a WT1 gene at high levels, and the cytotoxic activity of such CTLs is HLA-A2-restricted (Non-patent Document 11). It was shown in in vitro experiments in human cells using WT1 peptide that matches HLA-A*2402 (which is found most frequently in Japanese people among HLA-A alleles) (WT1$_{235}$; amino acids 235-243 of SEQ ID No: 1, CMTWNQMNL) that WT1-specific CTLs (TAK-1) are induced (Non-patent Document 12), and the induced CTLs do not suppress the colony-forming activity of normal hematopoietic stem cells which partially express physiologically a WT1 gene (Non-patent Documents 13 and 14). These reports strongly suggest that not only in mice but also in human beings, WT1-specific CTLs can be induced, such CTLs have a cytotoxic activity against tumor cells expressing a WT1 gene at high levels, but do not have a cytotoxic activity against normal cells expressing physiologically a WT1 gene (Non-patent Documents 7, 10, 11, 12, 13 and 14).

The WT1 gene product is present as a nuclear protein, and is processed by proteasomes in cytoplasm to be fragmented into peptides. The fragmented peptides are transported into endoplasmic reticulum lumen by TAP (transporter associated with antigen processing) molecules, form complexes with MHC class I molecules, and are presented on the surfaces of cells. WT1-specific CTLs are induced as a result of recognition of WT1 peptide-MHC class I molecule complexes by CTL precursor cells via TCR, thereby exerting a cytotoxic effect on tumor cells presenting a WT1 gene product through MHC class I molecules (Non-patent Documents 7, 8 and 9). Then, it is required at least that a WT1 peptide used in cancer immunotherapy targeting a WT1 gene product is in the form that binds to an MHC class I molecule in a living body. However, MHC class I molecules are diverse and amino acid sequences of the WT1 peptides binding to respective MHC class I molecules are different from each other. Therefore, it is required to provide a peptide matching each subtype of MHC class I. However, only HLA-A*2402 molecule-, HLA-A*0201 molecule- and HLA-A*2601 molecule-restricted peptides are known as HLA molecule-restricted WT1 peptides to date (Patent Document 1, Non-patent Document 11 and Patent Document 2, respectively). HLA-A*3303 is present at next highest percentage to HLA-A*2402 in Japanese. Therefore, there is a need to find an HLA-A*3303-restricted WT1 peptide.

Patent Document 1: WO 2003/106682
Patent Document 2: WO 2005/095598
Non-patent Document 1: Daniel A. Haber et al., Cell. 1990 Jun. 29; 61(7):1257-69.
Non-patent Document 2: Call K M et al., Cell. 1990 Feb. 9; 60(3):509-20.
Non-patent Document 3: Menke A L et al., Int Rev Cytol. 1998; 181:151-212. Review.
Non-patent Document 4: Yamagami T et al., Blood. 1996 Apr. 1; 87(7):2878-84.
Non-patent Document 5: Inoue K et al., Blood. 1998 Apr. 15; 91(8):2969-76.
Non-patent Document 6: Tsuboi A et al., Leuk Res. 1999 May; 23(5):499-505.
Non-patent Document 7: Oka Y et al., J. Immunol. 2000 Feb. 15; 164(4):1873-80.
Non-patent Document 8: Melief C J et al., Immunol Rev. 1995 June; 145:167-77.
Non-patent Document 9: Ritz J, J Clin Oncol. 1994 February; 12(2):237-8.
Non-patent Document 10: Tsuboi A et al., J Clin Immunol. 2000 May; 20(3):195-202.
Non-patent Document 11: Oka Y et al., Immunogenetics. 2000 February; 51(2):99-107.
Non-patent Document 12: Ohminami H et al., Blood. 2000 Jan. 1; 95(1):286-93.

Non-patent Document 13: Gao L et al., Blood. 2000 Apr. 1; 95(7):2198-203.
Non-patent Document 14: Ohminami H et al., Blood. 2000 Jan. 1; 95(1):286-93.

DISCLOSURE OF INVENTION

Problems to be Solved by the Invention

The problems to be solved by the present invention are to provide an HLA-A*3303-restricted WT1 peptide, and a polynucleotide encoding the same, as well as a pharmaceutical composition for the treatment/prevention of a cancer comprising the same, and the like.

Means to Solve the Problems

As a result of intensive studies in view of the situation as described above, the present inventor has found that a peptide comprising an amino acid sequence consisting of 9 contiguous amino acids from a WT1 protein, wherein an amino acid at position 2 of the amino acid sequence is selected from the group consisting of Ala, Ile, Leu, Val, Phe, Tyr, Ser and Asp, and an amino acid at position 9 of the amino acid sequence is Arg can induce a WT1-specific CTL with a high rate. Thus, the present invention has been completed.

The present invention provide:

(1) a peptide comprising an amino acid sequence consisting of 9 contiguous amino acids from a WT1 protein, wherein an amino acid at position 2 of the amino acid sequence is selected from the group consisting of Ala, Ile, Leu, Val, Phe, Tyr, Ser and Asp, and an amino acid at position 9 of the amino acid sequence is Arg:

(2) the peptide according to (1), wherein the amino acid sequence is selected from the group consisting of:

```
                                      (SEQ ID No: 2)
    Leu Ser His Leu Gln Met His Ser Arg, (SEQ ID No: 3)
    Phe Ser Arg Ser Asp Gln Leu Lys Arg, (SEQ ID No: 4)
    Ser Asp Gln Leu Lys Arg His Gln Arg,
    and (SEQ ID No: 5)
    Thr Ser Glu Lys Pro Phe Ser Cys Arg;
```

(3) the peptide according to (2), wherein the amino acid sequence is Ser Asp Gln Leu Lys Arg His Gln Arg (SEQ ID No: 4);

(4) a pharmaceutical composition for the treatment or prevention of a cancer, comprising the peptide according to (1);

(5) a method for the treatment or prevention of a cancer, comprising administering an effective amount of the pharmaceutical composition according to (4) to an HLA-A*3303-positive subject;

(6) use of the peptide according to (1) for the manufacture of the pharmaceutical composition according to (4);

(7) a polynucleotide encoding the peptide according to (1);

(8) an expression vector comprising the polynucleotide according to (7);

(9) a pharmaceutical composition for the treatment or prevention of a cancer, comprising the polynucleotide according to (7) or the vector according to (8);

(10) a method for the treatment or prevention of a cancer, comprising administering an effective amount of the pharmaceutical composition according to (9) to an HLA-A*3303-positive subject;

(11) use of the polynucleotide according to (7) or the vector according to (8) for the manufacture of the pharmaceutical composition according to (9);

(12) a WT1-specific CTL, which is inducible by the peptide according to (1);

(13) a method for the induction of a WT1-specific CTL, comprising culturing a peripheral blood mononuclear cell in the presence of the peptide according to (1) to induce the WT1-specific CTL from the peripheral blood mononuclear cell;

(14) a kit for the induction of a WT1-specific CTL, comprising the peptide according to (1) as an essential component;

(15) an antigen-presenting cell presenting a WT1 peptide, which is inducible by the peptide according to (1);

(16) a method for the induction of an antigen-presenting cell presenting a WT1 peptide, comprising culturing an immature antigen-presenting cell in the presence of the peptide according to (1) to induce the antigen-presenting cell presenting a WT1 peptide from the immature antigen-presenting cell;

(17) a kit for the induction of an antigen-presenting cell presenting a WT1 peptide, comprising the peptide according to (1) as an essential component;

(18) a method for the diagnosis of a cancer, comprising using the CTL according to (12) or the antigen-presenting cell according to (15);

(19) a method for the determination of the presence or amount of a WT1-specific CTL in an HLA-A*3303-positive subject, comprising:

(a) reacting a complex of a WT1 peptide and an HLA-A*3303 molecule with a sample from the subject; and (b) determining the presence or amount of a CTL recognizing the complex contained in the sample; and

(20) the method according to (19), wherein the complex is a form of tetramer.

Effects of the Invention

The present invention provides an HLA-A*3303-restricted WT1 peptide, and a polynucleotide encoding the same, as well as a pharmaceutical composition for the treatment or prevention of a cancer comprising the same, and the like. Therefore, it is possible to induce in vivo and in vitro WT1-specific CTLs in subjects having HLA-A*3303. Because about 240 of Japanese people have at least one HLA-A*3303 molecule, WT1-specific CTLs can be induced in a very wide range of subjects.

BEST MODE FOR CARRYING OUT THE INVENTION

Figure 1:
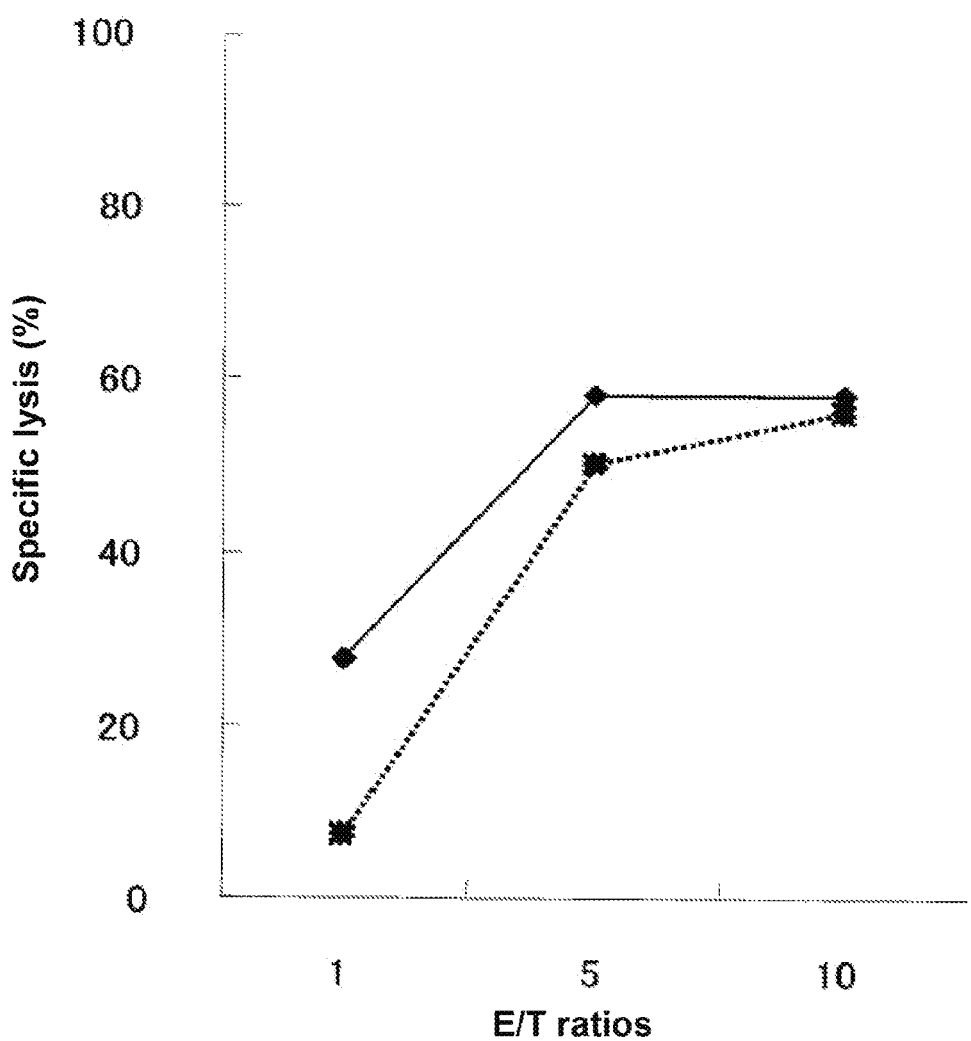
FIG. 1 represents the cytotoxic activity of the CTL induced with $WT1_{337}$.
Figure 2:
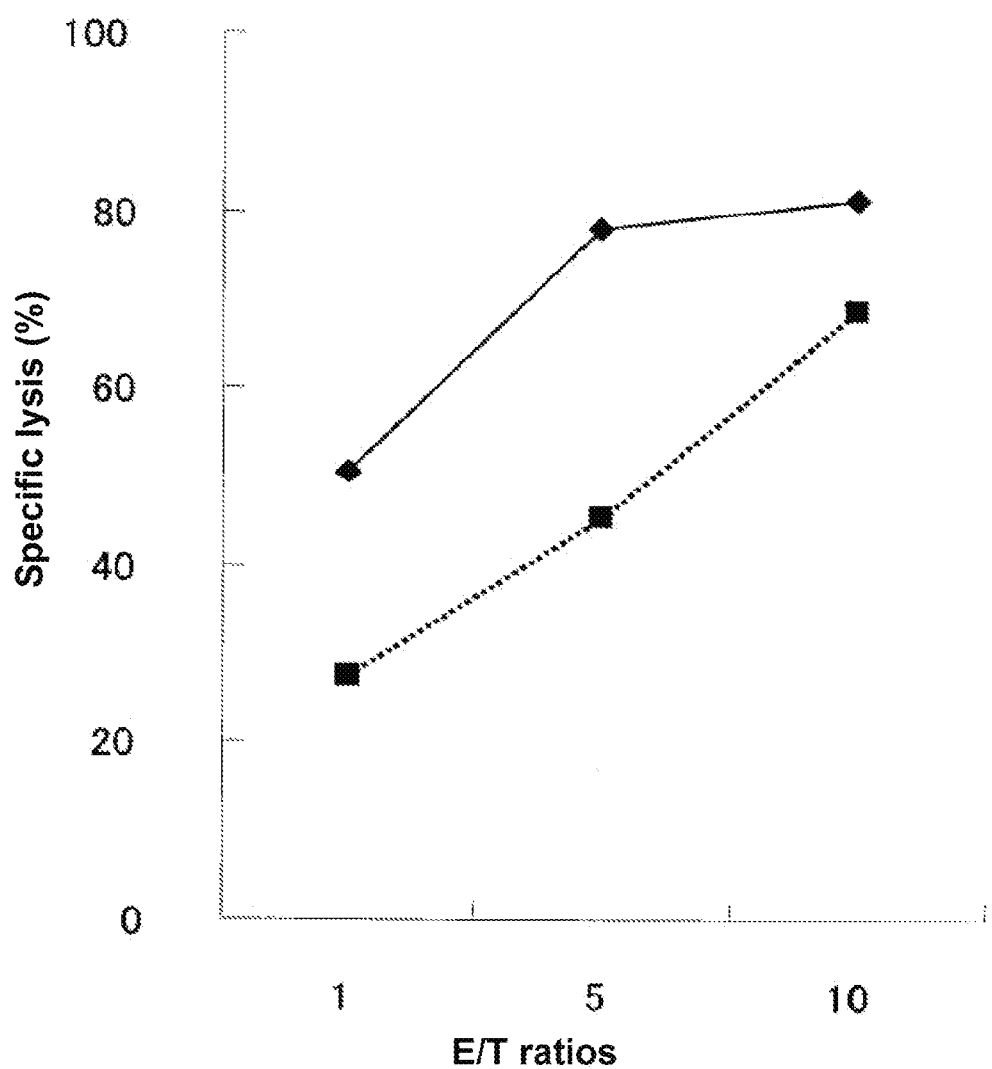
FIG. 2 represents the cytotoxic activity of the CTL induced with $WT1_{364}$.
Figure 3:
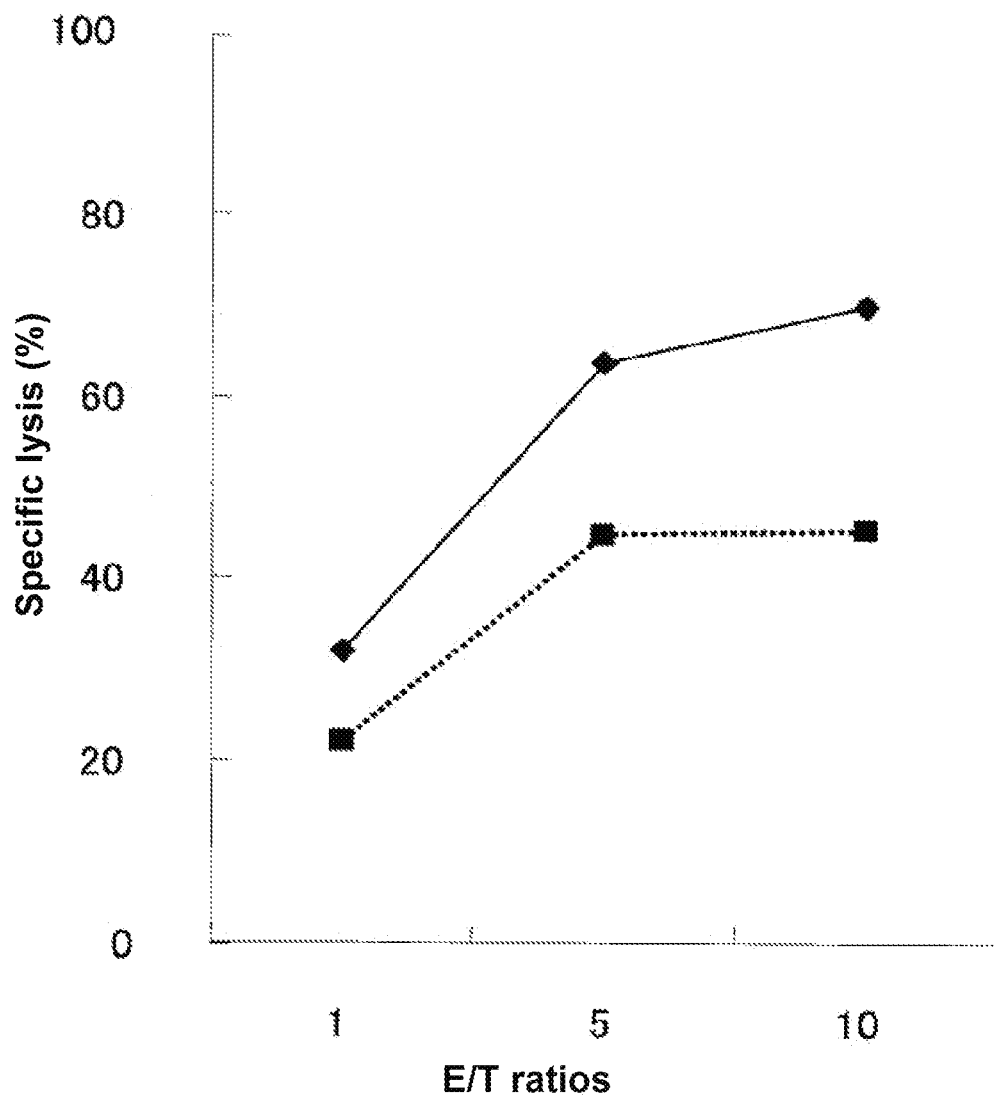
FIG. 3 represents the cytotoxic activity of the CTL induced with $WT1_{367}$.
Figure 4:
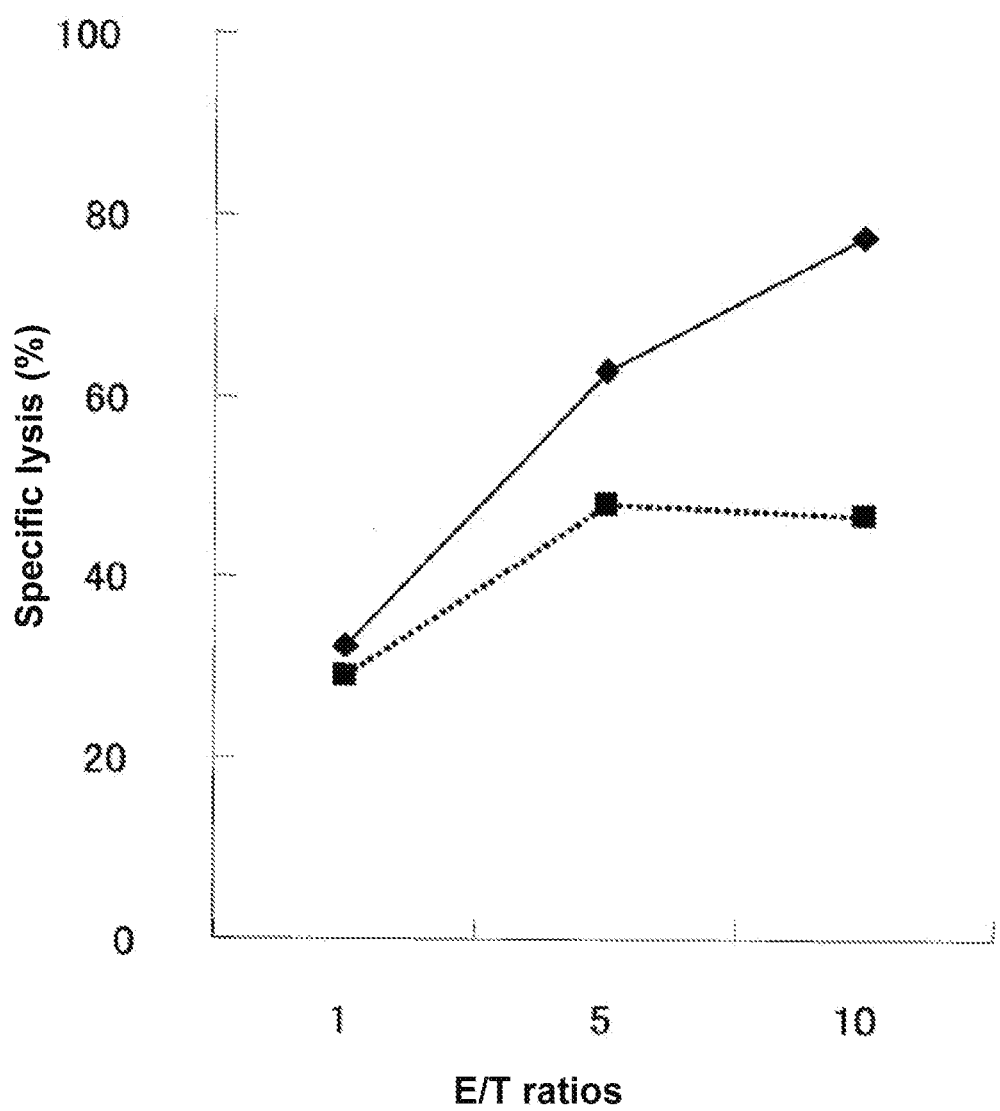
FIG. 4 represents the cytotoxic activity of the CTL induced with $WT1_{409}$.

An amino acid sequence of a human WT1 protein is shown in SEQ ID No: 1. A WT1 gene is expressed in its native form at high levels, for example, in hematopoietic tumors such as leukemia, myelodysplastic syndrome, multiple myeloma or malignant lymphoma and solid cancers such as gastric cancer, colon cancer, lung cancer, breast cancer, germ cell cancer, hepatic cancer, skin cancer, bladder cancer, prostate cancer, uterine cancer, cervical cancer or ovarian cancer. Furthermore, an anchor motif for HLA-A*3303 is characterized in that an amino acid at position 2 is any one of Ala, Ile, Leu, Val, Phe, Tyr, Ser and Asp, and an amino acid at position 9 is Arg. Thus, in one aspect, the present invention relates to an HLA-A*3303-restricted WT1 peptide comprising an amino acid sequence consisting of 9 contiguous amino acids from a WT1 protein, wherein an amino acid at position 2 of the amino acid sequence is preferably selected from the group consisting of Ala, Ile, Leu, Val, Phe, Tyr, Ser and Asp, and an amino acid at position 9 of the amino acid sequence is preferably Arg (hereinafter referred to as a WT1 peptide).

The amino acid sequence consisting of 9 amino acids comprised in the peptide of the present invention is preferably, Leu Ser H is Leu Gln Met H is Ser Arg (SEQ ID No: 2), Phe Ser Arg Ser Asp Gln Leu Lys Arg (SEQ ID No: 3), Ser Asp Gln Leu Lys Arg H is Gln Arg (SEQ ID No: 4) or Thr Ser Glu Lys Pro Phe Ser Cys Arg (SEQ ID No: 5). Most preferably, it is Ser Asp Gln Leu Lys Arg H is Gln Arg (SEQ ID No: 4). Furthermore, it may have a substitution of one to several, preferably one to five amino acids with other amino acids in the 9 amino acids of any of SEQ ID Nos: 2-5. Any one of the 9 amino acids or other substituted amino acids may be appropriately modified. In any cases, the peptide of the present invention retains an ability to bind to an HLA-A*3303 molecule.

As described above, it is an object of the present invention to obtain an HLA-A*3303-restricted WT1 peptide. Thus, the peptide of the present invention may be any one as long as it comprises an amino acid sequence that is derived from a WT1 protein and consists of 9 contiguous amino acids. Thus, the peptide of the present invention may be, for example, a peptide consisting of only the amino acid sequence shown in any of SEQ ID Nos: 2-5, or a WT1 protein or a part thereof comprising the amino acid sequence shown in any of SEQ ID Nos: 2-5. Various substances may be attached at the N-terminus and/or the C-terminus of the amino acid sequence consisting of 9 contiguous amino acids in the peptide of the present invention. For example, an amino acid, a peptide or an analog thereof may be attached. If these substances are attached to the peptide of the present invention, they can be processed, for example, by an enzyme in a living body or through a process such as intracellular processing, and finally the amino acid sequence consisting of 9 contiguous amino acids can be produced and presented as a complex with an HLA-A*3303 molecule on the surface of a cell, thereby resulting in the effect of inducing a CTL. These substances may be those which modulate the solubility of the peptides of the present invention, or increase their stability (resistance to protease, etc.). Alternatively, these substances may be those which deliver the peptides of the present invention specifically, for example, to a given tissue or organ, or they may have the action to increase the efficiency of uptake by an antigen-presenting cell or the like. These substances may be those which increase the ability to induce a CTL, such as helper peptides or the like.

The peptide of the present invention can be synthesized by methods generally used in the art or modifications thereof. Such methods are described, for example, in Peptide Synthesis, Interscience, New York, 1966; The Proteins, Vol 2, Academic Press Inc., New York, 1976; Peptide-Gosei, Maruzen Co., Ltd., 1975; Peptide-Gosei No Kiso To Jikken, Maruzen Co., Ltd., 1985; and Iyakuhin No Kaihatsu (Zoku), Vol. 14, Peptide-Gosei, Hirokawa—Book store, 1991.

The peptide of the present invention can also be prepared using genetic engineering techniques based on the information about the nucleotide sequence that encodes the peptide of the present invention. Such genetic engineering techniques are well known to a person skilled in the art.

In another aspect, the present invention relates to a pharmaceutical composition for the treatment or prevention of a cancer, comprising the HLA-A*3303-restricted WT1 peptide. The WT1 gene is expressed at high levels in hematopoietic tumors such as leukemia, myelodysplastic syndrome, multiple myeloma or malignant lymphoma, and solid cancers such as gastric cancer, colon cancer, lung cancer, breast cancer, germ cell cancer, hepatic cancer, skin cancer, bladder cancer, prostate cancer, uterine cancer, cervical cancer or ovarian cancer. Therefore, the pharmaceutical composition of the present invention can be used for the treatment or prevention of a cancer. When the pharmaceutical composition of the present invention is administered to an HLA-A*3303-positive subject, WT1-specific CTLs are induced by the HLA-A*3303-restricted WT1 peptide comprised in the pharmaceutical composition, and cancer cells in the subject are damaged by such CTLs.

The pharmaceutical composition of the present invention may comprise in addition to the HLA-A*3303-restricted WT1 peptide as an active ingredient, for example, a carrier, an excipient or the like. The HLA-A*3303-restricted WT1 peptide comprised in the pharmaceutical composition of the present invention induces a WT1-specific CTL. Thus, the pharmaceutical composition of the present invention may comprise an appropriate adjuvant, or may be administered together with an appropriate adjuvant in order to enhance the induction efficiency. Examples of preferable adjuvants include, but are not limited to, complete or incomplete Freund's adjuvant and aluminum hydroxide.

The method of the administration of the pharmaceutical composition of the present invention can be appropriately selected depending on conditions such as the type of disease, the condition of the subject or the target site. Examples of such methods include, but are not limited to, intradermal administration, subcutaneous administration, intramuscular administration, intravenous administration, nasal administration and oral administration. The amount of the peptide comprised in the pharmaceutical composition of the present invention, as well as the dosage form, the number of times of the administration and the like of the pharmaceutical composition of the present invention can be appropriately selected depending on conditions such as the type of disease, the condition of the subject or the target site.

The single dose of the peptide is usually, 0.0001 mg-10000 mg, preferably, 0.001 mg-1000 mg.

In another aspect, the present invention relates to a method for the treatment or prevention of a cancer, comprising administering an effective amount of the pharmaceutical composition to an HLA-A*3303-positive subject. The cancer to be treated or prevented may be any one, and examples thereof include hematopoietic tumors such as leukemia, myelodysplastic syndrome, multiple myeloma or malignant lymphoma and solid cancers such as gastric cancer, colon cancer, lung cancer, breast cancer, germ cell cancer, hepatic cancer, skin cancer, bladder cancer, prostate cancer, uterine cancer, cervical cancer or ovarian cancer.

In another aspect, the present invention relates to use of an HLA-A*3303-restricted WT1 peptide for the manufacture of the pharmaceutical composition.

In a further aspect, the present invention relates to a method for the determination of the presence or amount of a WT1-specific CTL in an HLA-A*3303-positive subject, comprising:
(a) reacting a complex of a WT1 peptide and an HLA-A*3303 molecule with a sample form the subject; and
(b) determining the presence or amount of a CTL recognizing the complex contained in the sample. The sample from a subject may be any one as long as there is a possibility that it contains a lymphocyte. Examples of the samples include body fluid such as blood or lymph and a tissue. The complex of a WT1 peptide and an HLA-A*3303 molecule may be prepared, for example, as a tetramer or pentamer using a method known to a person skilled in the art such as biotin-streptavidin method. The presence or amount of the CTL recognizing such a complex can be measured by a method known to a person skilled in the art. In this aspect of the present invention, the complex may be labeled. A known label such as a fluorescent label or a radioactive label can be used as a label. Labeling makes the determination of the presence or amount of a CTL easy and rapid. The method of this aspect of the present invention can be used to diagnose a cancer, prognosis thereof or the like.

Thus, the present invention also provides a composition for the determination of the presence or amount of a WT1-specific CTL in an HLA-A*3303-positive subject, comprising a complex of a WT1 peptide and an HLA-A*3303 molecule.

Furthermore, the present invention provides a kit for the determination of the presence or amount of a WT1-specific CTL in an HLA-A*3303-positive subject, comprising a complex of a WT1 peptide and an HLA-A*3303 molecule.

In a further aspect, the present invention relates to a method for the production of a WT1-specific CTL using a complex of a WT1 peptide and an HLA-A*3303 molecule, comprising:
(a) reacting the complex with a sample; and
(b) obtaining a CTL recognizing the complex contained in the sample. The complex of a WT1 peptide and an HLA-A*3303 molecule is described above. The sample may be any one as long as there is a possibility that it contains a lymphocyte. Examples of the samples include a sample from a subject such as blood, and a cell culture. The CTL recognizing the complex can be obtained using a method known to a person skilled in the art such as FACS or MACS. The present invention allows to culture the obtained WT1-specific CTL and use it for the treatment or prevention of various cancers.

Thus, the present invention also relates to a WT1-specific CTL which is obtainable by a method for the production of a WT1-specific CTL using a complex of a WT1 peptide and an HLA-A*3303 molecule.

Furthermore, the present invention relates to a kit for the production of a WT1-specific CTL, comprising a complex of a WT1 peptide and an HLA-A*3303 molecule.

In another aspect, the present invention relates to a polynucleotide encoding the HLA-A*3303-restricted WT1 peptide (hereinafter referred to as a WT1 polynucleotide). The polynucleotide of the present invention may be DNA or RNA. The base sequence of the polynucleotide of the present invention can be determined based on the amino acid sequence of the HLA-A*3303-restricted WT1 peptide. The polynucleotide can be prepared, for example, by a method for the synthesis of DNA or RNA, PCR method or the like.

In another aspect, the present invention relates to an expression vector comprising the polynucleotide (hereinafter referred to as a WT1 expression vector). The type of the expression vector, the comprised sequence other than the sequence of the polynucleotide and the like can be appropriately selected depending on the type of a host into which the expression vector of the present invention is introduced, the purpose of use, or the like. It is possible to treat or prevent hematopoietic tumors or solid cancers by administering the expression vector of the present invention to an HLA-A*3303-positive subject to produce a WT1 peptide in a living body and induce a WT1-specific CTL, and damaging hematopoietic tumor cells or solid cancer cells in the subject.

In another aspect, the present invention relates to a pharmaceutical composition for the treatment or prevention of a cancer, comprising the WT1 polynucleotide or the WT1 expression vector. The composition, the method of the administration and the like of the pharmaceutical composition of the present invention in this aspect are described above.

In another aspect, the present invention relates to a method for the treatment or prevention of a cancer, comprising administering an effective amount of the pharmaceutical composition comprising the WT1 peptide or the WT1 expression vector to an HLA-A*3303-positive subject. Examples of cancers to be treated or prevented include hematopoietic tumors such as leukemia, myelodysplastic syndrome, multiple myeloma or malignant lymphoma and solid cancers such as gastric cancer, colon cancer, lung cancer, breast cancer, germ cell cancer, hepatic cancer, skin cancer, bladder cancer, prostate cancer, uterine cancer, cervical cancer or ovarian cancer.

In another aspect, the present invention relates to use of a WT1 polynucleotide or a WT1 expression vector for the manufacture of the pharmaceutical composition comprising the WT1 polynucleotide or the WT1 expression vector.

In another aspect, the present invention relates to a cell comprising the expression vector. The cell of the present invention can be prepared, for example, by transforming a host cell such as *E. coli*, yeast, insect cell or animal cell with the expression vector. The method for the introduction of the expression vector into a host cell can be appropriately selected from various methods. By culturing the transformed cell, and recovering and purifying the produced WT1 peptide, the peptide of the present invention can be prepared.

In a further aspect, the present invention relates to a WT1-specific CTL, which is induced by the HLA-A*3303-restricted WT1 peptide. The CTL of the present invention recognizes a complex of a WT1 peptide and an HLA-A*3303 molecule. Thus, the CTL of the present invention can be used to damage specifically a tumor cell positive for HLA-A*3303 and expressing WT1 at a high level.

In another aspect, the present invention relates to a method for the treatment or prevention of a cancer, comprising administering a WT1-specific CTL to an HLA-A*3303-positive subject. The method of the administration of the WT1-specific CTL can be appropriately selected depending on conditions such as the type of the disease, the condition of the subject or the target site. Examples of such methods include, but are not limited to, intravenous administration, intradermal administration, subcutaneous administration, intramuscular administration, nasal administration and oral administration.

In another aspect, the present invention relates to a method for the induction of a WT1-specific CTL, comprising culturing a peripheral blood mononuclear cell in the presence of the HLA-A*3303-restricted WT1 peptide to induce the WT1-specific CTL form the peripheral blood mononuclear cell. The subject from which the peripheral blood mononuclear cell is derived may be any one as long as it is positive for HLA-A*3303. By culturing the peripheral blood mononuclear cells in the presence of the HLA-A*3303-restricted WT1 peptide, WT1-specific CTLs are induced from CTL precursor cells contained in the peripheral blood mononuclear cells. It is possible to treat or prevent hematopoietic tumors or solid cancers in an HLA-A*3303-positive subject by administering the WT1-specific CTL obtained according to the present invention to the subject.

In another aspect, the present invention relates to a kit for the induction of a WT1-specific CTL, comprising an HLA-A*3303-restricted WT1 peptide as an essential component. Preferably, the kit is used in the method for the induction of a WT1-specific CTL. The kit of the present invention may comprise in addition to the HLA-A*3303-restricted WT1 peptide, for example, a means of obtaining a peripheral blood mononuclear cell, an adjuvant, a reaction vessel or the like. In general, an instruction manual is attached to the kit. By using the kit of the present invention, WT1-specific CTLs can be induced efficiently.

In a further aspect, the present invention relates to an antigen-presenting cell (such as a dendritic cell) presenting a WT1 peptide through an HLA-A*3303 molecule, which is induced by the HLA-A*3303-restricted WT1 peptide. By using the antigen-presenting cell of the present invention, WT1-specific CTLs are induced efficiently.

In another aspect, the present invention relates to a method for the treatment or prevention of a cancer, comprising administering the antigen-presenting cell presenting a WT1 peptide through an HLA-A*3303 molecule to an HLA-A*3303-positive subject. The method of the administration of the antigen-presenting cell can be appropriately selected depending on conditions such as the type of the disease, the condition of the subject or the target site. Examples of such methods include, but are not limited to, intravenous administration, intradermal administration, subcutaneous administration, intramuscular administration, nasal administration and oral administration.

In another aspect, the present invention relates to a method for the induction of an antigen-presenting cell presenting a WT1 peptide through an HLA-A*3303 molecule, comprising culturing an immature antigen-presenting cell in the presence of the HLA-A*3303-restricted WT1 peptide to induce the antigen-presenting cell presenting a WT1 peptide through an HLA-A*3303 molecule from the immature antigen-presenting cell. The immature antigen-presenting cell refers a cell such as an immature dendritic cell that can be matured into an antigen-presenting cell. A subject from which the immature antigen-presenting cell is derived may be any one as long as it is positive for HLA-A*3303. Because the immature antigen-presenting cells are contained, for example, in peripheral blood mononuclear cells, such cells may be cultured in the presence of the WT1 peptide.

In another aspect, the present invention relates to a kit for the induction of an antigen-presenting cell presenting a WT1 peptide through an HLA-A*3303 molecule, comprising the HLA-A*3303-restricted WT1 peptide as an essential component. Preferably, the kit is used in the method for the induction of an antigen-presenting cell. Another component to be comprised in the kit of the present invention and the like are described above. The kit of the present invention can be used to induce efficiently an antigen-presenting cell presenting a WT1 peptide through an HLA-A*3303 molecule.

In another aspect, the present invention relates to an antibody against an HLA-A*3303-restricted WT1 peptide or an antibody against a polynucleotide encoding the peptide. The antibody of the present invention may be a polyclonal antibody or monoclonal antibody.

In a further aspect, the present invention relates to a method for the diagnosis of a cancer, comprising using the WT1-specific CTL, the antigen-presenting cell presenting a WT1 peptide through an HLA-A*3303 molecule, or the antibody against an HLA-A*3303-restricted WT1 peptide or the antibody against a polynucleotide encoding the peptide. Preferably, the WT1-specific CTL is used in the method for the diagnosis of the present invention. For example, it is possible to diagnose a cancer by incubating the CTL, the antigen-presenting cell or the antibody with a sample from an HLA-A*3303-positive subject, or administering it to an HLA-A*3303-positive subject, and determining, for example, the position, site or amount thereof. The CTL, the antigen-presenting cell or the antibody may be labeled. By attaching a label, the method for the diagnosis of the present invention can be practiced efficiently.

In another aspect, the present invention relates to a kit for the diagnosis of a cancer, comprising the WT1-specific CTL, the antigen-presenting cell presenting a WT1 peptide through an HLA-A*3303 molecule, or the antibody against an HLA-A*3303-restricted WT1 peptide or the antibody against a polynucleotide encoding the peptide as an essential component.

The following examples illustrate the present invention in more detail, but are not to be construed to limit the scope thereof.

EXAMPLES

Example 1

Selection of WT1 peptide

NetMHC2.0 Program (Technical University of Denmark) was used to select $WT1_{337}$, $WT1_{364}$, $WT1_{367}$ and $WT1_{409}$, which are hydrophilic peptides consisting of 9 amino acids with the anchor motif suitable for HLA-A*3303 (the second amino acid from the N-terminus is any one of Ala, Ile, Leu, Val, Phe, Tyr, Ser and Asp, and the amino acid at the C-terminus is Arg) and are expected to have a high binding affinity to an HLA-A*3303 molecule from a WT1 peptide from a WT1 protein (SEQ ID No: 1). Amino acid sequences and the binding affinities to an HLA-A*3303 molecule of these peptides are shown in Table 1.

TABLE 1

| Peptide | Amino acid Number in SEQ ID NO: 1 | Amino sequence | Binding affinity to HLA-A*3303 molecule |
|---|---|---|---|
| $WT1_{337}$ (SEQ ID No: 2) | 337-345 | LSHLQMHSR | 18.827 |
| $WT1_{364}$ (SEQ ID No: 3) | 364-372 | FSRSDQLKR | 15.143 |
| $WT1_{367}$ (SEQ ID No: 4) | 367-375 | SDQLKRHQR | 14.496 |
| $WT1_{409}$ (SEQ ID No: 5) | 409-417 | TSEKPFSCR | 15.310 |

Preparation of B-LCL Cell

Peripheral blood mononuclear cells (PBMCs) were separated by Ficoll-Hypaque gradient density centrifugation method from peripheral blood that had been collected from an HLA-A*3303-positive healthy donor (HLA-A*3303/0207). The PBMCs were then seeded to a 24-well cell culture plate at the density of about $1\times10^7$ in RPMI 1640 medium containing 10% FCS, and a culture supernatant of B95-8 cells (cells producing EB virus) were added. They were cultured at 37° C. with 5% $CO_2$ for about 1 month. B-LCL cells transformed with EB virus, which are B-cell tumor cells, were obtained. It was confirmed that the resulting B-LCL cells did not express WT1 gene. B-LCL cells were pulsed by incubating them with 20 μg/ml of WT1$_{337}$, WT1$_{364}$, WT1$_{367}$ or WT1$_{409}$ for 2 hours, and irradiated with 80 Gy of radiation. The resulting B-LCL cells (hereinafter referred to as B-LCL cells pulsed with a WT1 peptide) were used as antigen-presenting cells for the following experiments.

Induction of CTL Specific WT1

3×10$^6$ of PBMCs (HLA-A*3303/1101) were cultured in a 24-well cell culture plate in complete medium (450 RPMI, 45% AMI-V medium and 10% human AB serum) containing 20 μg/ml of WT1$_{337}$, WT1$_{364}$, WT1$_{367}$ or WT1$_{409}$ at 37° C. with 5% CO$_2$ for 1 week to obtain responding cells. 2×10$^6$ of the resulting responding cells were cocultured with 1×10$^6$ of the B-LCL cells pulsed with the same WT1 peptide in complete medium for 1 week (first stimulation). The PBMCs were cocultured with the B-LCL cells pulsed with the WT1 peptide three more times (second to fourth stimulations) under the conditions under which 20 IU/ml (final concentration) of IL-2 was added as follows: second stimulation: two times every other day from 3 days after the initiation of stimulation; third and fourth stimulations: three times at intervals of one day from the day after the initiation of stimulation. The resulting cells were concentrated using Negative Selection Columns Gravity Feed Kit (StemSp) so that the ratio of CD8-positive T cells became about 800, and cocultured with the B-LCL cells pulsed with the WT1 peptide (fifth stimulation). CD8-positive T cells (CTLs) obtained 5 days after the final stimulation were used for measurement of the cytotoxic activity.

Cytotoxic Activity of CTL

The cytotoxic activity of CTLs was measured using $^{51}$Cr release assay. CTL cells (hereinafter referred to as effector cells) were mixed at the ratio (E/T ration) of 1:1, 5:1 or 10:1 in 200 μl of medium with target cells into which $^{51}$Cr had been incorporated, and cultured in a 96-well cell culture plate at 37° C. with 5% CO$_2$ for 4 hours. B-LCL cells pulsed with the same WT1 peptide as that used for induction of CTLs (BLCL-Ps), and B-LCL cells without pulsing with a WT1 peptide (BLCL-NPs) were used as target cells. After the culture, the supernatants were collected by centrifugation. The amounts of $^{51}$Cr released into the supernatants were measured using a liquid scintillation counter. The cytotoxic activity (%) was determined using the following formula:

($^{51}$Cr release in supernatant of sample−Spontaneous $^{51}$Cr release)/(Maximum $^{51}$Cr release−Spontaneous $^{51}$Cr release)×100 wherein Spontaneous $^{51}$Cr release is $^{51}$Cr release observed when the target cells into which $^{51}$Cr had been incorporated were cultured alone under the same condition, and Maximum $^{51}$Cr release is $^{51}$Cr release observed when the target cells into which $^{51}$Cr had been incorporated were completely lysed using 1% Triton X-100. Results are shown in FIGS. 1-4. In the figures, longitudinal axes represent specific lysis (%), and horizontal axes represent E/T ratios. BLCL-Ps are represented using full lines, and BLCL-NPs are represented using dotted lines. It was confirmed that CTLs induced with WT1$_{337}$, WT1$_{364}$, WT1$_{367}$ or WT1$_{409}$ damage specifically BLCL-Ps presenting the WT1 peptide as a complex with an HLA-A*3303 molecule as compared with BLCL-NPs. CTLs induced with WT1$_{364}$, WT1$_{367}$ or WT1$_{409}$ were used for further experiments below.

Cytotoxic activity of CTL against cell expressing WT1 gene endogenously

Figure 5:
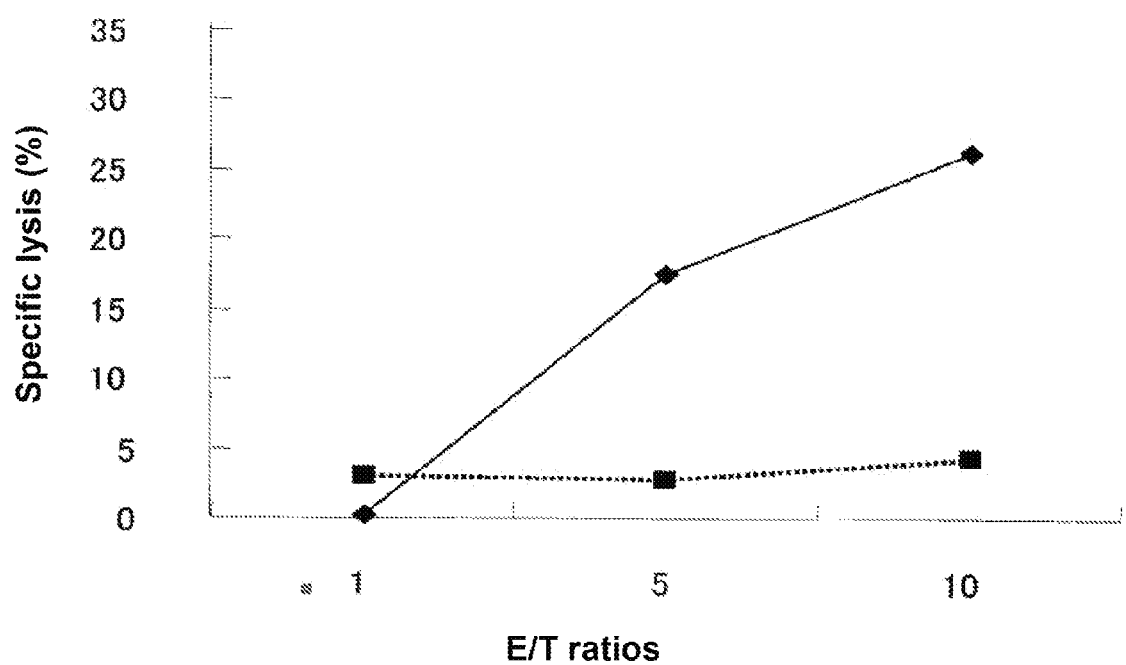
FIG. 5 represents the cytotoxic activity of the CTL induced with $WT1_{364}$ against the cell expressing a WT1 gene endogenously.
Figure 6:
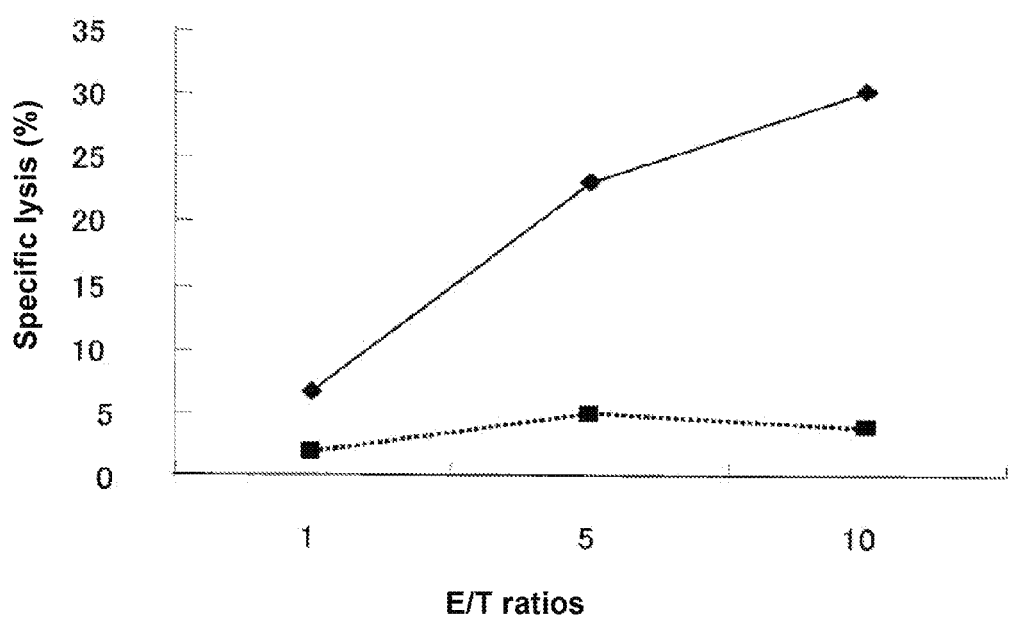
FIG. 6 represents the cytotoxic activity of the CTL induced with $WT1_{367}$ against the cell expressing a WT1 gene endogenously.
Figure 7:
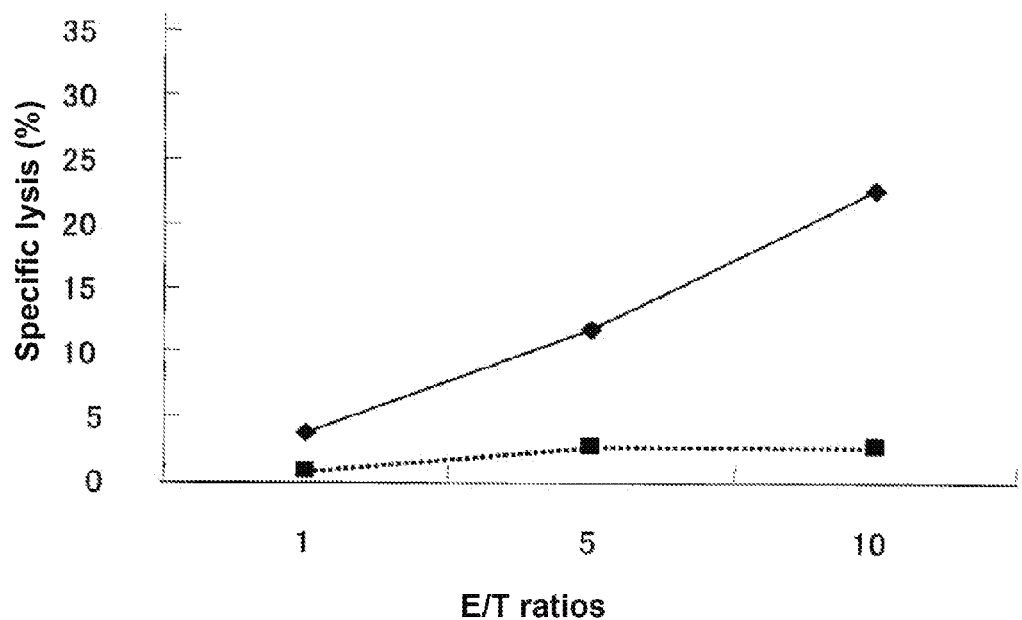
FIG. 7 represents the cytotoxic activity of the CTL induced with $WT1_{409}$ against the cell expressing a WT1 gene endogenously.

The cytotoxic activity of CTLs induced with WT1$_{364}$, WT1$_{367}$ or WT1$_{409}$ against TF-1 cells that are tumor cells expressing a WT1 gene (HLA-A*3303-positive) was determined using the method as described above. As a control, K562 cells that express a WT1 gene and are negative for HLA-A*3303 were used. Results are shown in FIGS. 5-7. In the figures, longitudinal axes represent specific lysis (%), and horizontal axes represent E/T ratios. TF-1 is represented using full lines, and K562 is represented using dotted lines. It was confirmed that CTLs induced with WT1$_{364}$, WT1$_{367}$ or WT1$_{409}$ also have a cytotoxic activity against the cell expressing a WT1 gene exogenously.

Figure 8:
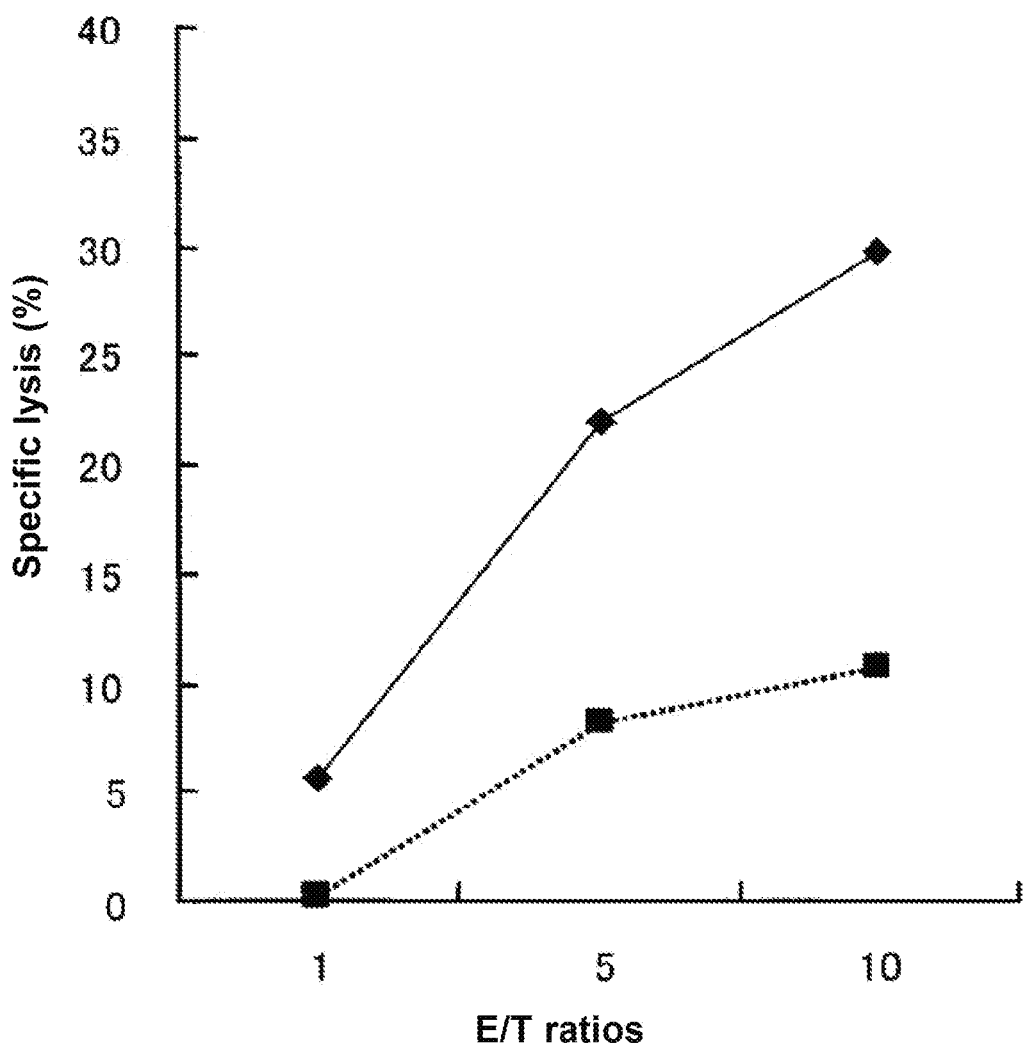
FIG. 8 represents the cytotoxic activity of the CTL induced with $WT1_{367}$ against the cell expressing a WT1 gene.

The cytotoxic activity of CTLs induced with WT1$_{367}$ against B-LCL cell expressing WT1 was determined using the method as described above. The B-LCL expressing WT1 (B-LCL-WT1) refers to B-LCL cell into which a human WT1 gene is introduced and expresses a WT1 protein in the cell, and presents a peptide consisting of about 9 amino acids resulting from processing on an HLA-A*3303 molecule. As a control, B-LCL cell (B-LCL-CV) into which a control gene except a WT1 gene is introduced was used. Results are shown in FIG. 8. In the figures, longitudinal axes represent specific lysis (%), and horizontal axes represent E/T ratios. B-LCL-WT1 is represented using full lines, and B-LCL-CV is represented using dotted lines. It was confirmed that CTLs induced with WT1$_{367}$ damage only the cell which is HLA-A*3303-positive and expresses WT1.

INDUSTRIAL APPLICABILITY

The present invention provides an HLA-A*3303-restricted WT1 peptide, a polynucleotide encoding the peptide, a pharmaceutical composition comprising the same and the like. Therefore, the present invention can be used in the fields of medicine and the like, for example, in the fields of development and preparation of a pharmaceutical composition for the prevention or treatment of various hematopoietic tumors and solid cancers that express WT1 gene at high levels.

The invention claimed is:

1. A method for the treatment of cancer in a human leukocyte antigen (HLA)-A*3303 positive subject, comprising administering to the subject an isolated peptide comprising Phe Ser Arg Ser Asp Gln Leu Lys Arg (SEQ ID NO: 3),
   wherein the peptide binds to an HLA-A*3303 molecule and induces a Wilms' tumor 1 (WT1)-specific cytotoxic T lymphocyte (CTLs) in the subject,
   wherein the cancer is selected from leukemia, myelodysplastic syndrome, multiple myeloma, malignant lymphoma, gastric cancer, colon cancer, lung cancer, breast cancer, germ cell cancer, hepatic cancer, skin cancer, bladder cancer, prostate cancer, uterine cancer, cervical cancer, and ovarian cancer, and
   wherein the peptide is administered via a route selected from the group consisting of intradermal, subcutaneous, intramuscular, intravenous, nasal and oral.

2. The method according to claim 1, further comprising administering to the subject an adjuvant with the peptide.

3. The method according to claim 2, wherein the adjuvant is selected from a complete Freund's adjuvant, an incomplete Freund's adjuvant, and aluminum hydroxide.

4. A method for the treatment of cancer in HLA-A*3303 positive subject, comprising administering to the subject an isolated peptide comprising Phe Ser Arg Ser Asp Gln Leu Lys Arg (SEQ ID NO: 3),
   wherein the peptide binds to an HLA-A*3303 molecule and induces WT1-specific CTLs in the subject,
   wherein the cancer is selected from leukemia, myelodysplastic syndrome, multiple myeloma, malignant lymphoma, gastric cancer, colon cancer, lung cancer, breast cancer, germ cell cancer, hepatic cancer, skin cancer, bladder cancer, prostate cancer, uterine cancer, cervical cancer, and ovarian cancer, and
   wherein the composition is administered via a route selected from the group consisting of intradermal, subcutaneous, intramuscular, intravenous, nasal and oral.

5. The method according to claim 4, wherein the pharmaceutical composition further comprises at least one second component.

6. The method according to claim 5, wherein the at least one second component is an adjuvant.

7. The method according to claim 6, wherein the adjuvant is selected from a complete Freund's adjuvant, an incomplete Freund's adjuvant, and aluminum hydroxide.

8. The method according to claim 4, further comprising administering to the subject a second agent with the pharmaceutical composition.

9. The method according to claim 8, wherein the second agent is an adjuvant.

10. The method according to claim 9, wherein the adjuvant is selected from a complete Freund's adjuvant, an incomplete Freund's adjuvant, and aluminum hydroxide.

11. The method according to claim 1, wherein the peptide consists of Phe Ser Arg Ser Asp Gln Leu Lys Arg (SEQ ID No: 3).

12. The method according to claim 4, wherein the peptide consists of Phe Ser Arg Ser Asp Gin Leu Lys Arg (SEQ ID No: 3).

* * * * *

UNITED STATES PATENT AND TRADEMARK OFFICE
CERTIFICATE OF CORRECTION

PATENT NO. : 8,933,038 B2  Page 1 of 1
APPLICATION NO. : 14/145221
DATED : January 13, 2015
INVENTOR(S) : Haruo Sugiyama It is certified that error appears in the above-identified patent and that said Letters Patent is hereby corrected as shown below:

In the Claims

In claim 12, column 17, line 2, "Gin" should read --Gln--.

Signed and Sealed this
Tenth Day of November, 2015

Michelle K. Lee
*Director of the United States Patent and Trademark Office*